US008581012B2

(12) United States Patent
Tirtowidjojo et al.

(10) Patent No.: US 8,581,012 B2
(45) Date of Patent: Nov. 12, 2013

(54) PROCESSES FOR THE PRODUCTION OF CHLORINATED AND/OR FLUORINATED PROPENES AND HIGHER ALKENES

(75) Inventors: Max M. Tirtowidjojo, Lake Jackson, TX (US); Patrick H. Au-Yeung, Midland, MI (US); Debashis Chakraborty, Lake Jackson, TX (US); Juergen Eiffler, Stade (DE); Heinz Groenewald, Hammah (DE); Kurt F. Hirsekorn, Midland, MI (US); Manfred Kokott, Stade (DE); William J. Kruper, Jr., Sanford, MI (US); Thomas U. Luebbe, Stade (DE); Holger Meemann, Stade (DE); Shirley S. Sexton, Cypress, TX (US); Peter Wenzel, Buxtehude (DE); Marcus Wobser, Stade (DE)

(73) Assignee: Dow Global Technologies, LLC, Midland, MI (US)

( * ) Notice: Subject to any disclaimer, the term of this patent is extended or adjusted under 35 U.S.C. 154(b) by 248 days.

(21) Appl. No.: 12/901,451

(22) Filed: Oct. 8, 2010

(65) Prior Publication Data

US 2011/0087055 A1    Apr. 14, 2011

Related U.S. Application Data

(60) Provisional application No. 61/250,024, filed on Oct. 9, 2009.

(51) Int. Cl.
 *C07C 17/20* (2006.01)
(52) U.S. Cl.
 USPC .......................................... 570/160; 570/159
(58) Field of Classification Search
 None
 See application file for complete search history.

(56) References Cited

U.S. PATENT DOCUMENTS

| | | | |
|---|---|---|---|
| 2,119,484 A | 5/1938 | Levine | |
| 2,299,441 A | 9/1939 | Vaughan | |
| 2,179,378 A | 11/1939 | Metzger | |
| 2,302,228 A | 11/1942 | Kharasch et al. | |
| 2,370,342 A | 2/1945 | Naeher | |
| 2,435,983 A | 12/1945 | Schmerling | |
| 2,449,286 A | 9/1948 | Fairbairn | |
| 2,630,461 A | 3/1953 | Sachsse | |
| 2,688,592 A | 9/1954 | Skeeters | |
| 2,765,359 A | 10/1956 | Pichler | |
| 2,973,393 A | 2/1961 | Monroe | |
| 3,000,980 A | 9/1961 | Asadorian | |
| 3,094,567 A | 6/1963 | Eaker | |
| 3,446,859 A | 5/1969 | Weil et al. | |
| 3,502,734 A | 3/1970 | Baird | |
| 3,558,438 A | 1/1971 | Schoenbeck | |
| 3,651,019 A | 3/1972 | Asscher | |
| 3,676,508 A | 7/1972 | Krekeler | |
| 3,819,731 A | 6/1974 | Pitt et al. | |
| 3,823,195 A | 7/1974 | Smith | |
| 3,872,664 A | 3/1975 | Lohmann | |
| 3,914,167 A | 10/1975 | Ivy et al. | |
| 3,926,758 A | 12/1975 | Smith | |
| 3,948,858 A | 4/1976 | Wiersum | |
| 3,954,410 A | 5/1976 | Pohl | |
| 4,051,182 A | 9/1977 | Pitt | |
| 4,513,154 A | 4/1985 | Kurtz | |
| 4,535,194 A | 8/1985 | Woodard | |
| 4,614,572 A | 9/1986 | Holbrook | |
| 4,650,914 A | 3/1987 | Woodard | |
| 4,661,648 A | 4/1987 | Franklin | |
| 4,702,809 A | 10/1987 | Mueller | |
| 4,714,792 A | 12/1987 | Mueller et al. | |
| 4,716,255 A | 12/1987 | Mueller | |
| 4,726,686 A | 2/1988 | Wolf | |
| 4,727,181 A | 2/1988 | Kruper | |
| 4,894,205 A | 1/1990 | Westerman et al. | |
| 4,902,393 A | 2/1990 | Mueller | |
| 5,057,634 A | 10/1991 | Webster | |
| 5,132,473 A | 7/1992 | Furutaka et al. | |
| 5,171,899 A | 12/1992 | Furutaka et al. | |
| 5,254,771 A | 10/1993 | Cremer et al. | |
| 5,254,772 A | 10/1993 | Dukat | |
| 5,315,044 A | 5/1994 | Furutaka et al. | |
| 5,414,166 A | 5/1995 | Kim et al. | |
| 5,684,219 A | 11/1997 | Boyce | |
| 5,811,605 A | 9/1998 | Tang et al. | |

(Continued)

FOREIGN PATENT DOCUMENTS

| | | |
|---|---|---|
| CH | 609022 A5 | 2/1979 |
| CN | 101492341 | 7/2009 |

(Continued)

OTHER PUBLICATIONS

Nikishin et al., "Reactions of Methanol and Ethanol with Tetrachloroethylene", N.D. Zelinskii Institute of Organic Chemistry, Academy of Sciences of the USSR, Translated from Izvestiya Akademii Nauk SSSR, Seriya Khimicheskaya, No. 12, pp. 2188-2192, Dec. 1966.
Kruper et al., "Synthesis of alpha Halocinnamate Esters via Solvolytic Rearrangement of Trichloroallyl Alcohols", J. Org. Chem, 1991, pp. 3323-3329, 1991.
Semenov et al., "Selectivity of Photochemical Chlorination of Chloromethane in the Liquid Phase", Viniti, 3405-84, Feb. 13, 1988.
Zhao et al., "Research Progress on Preparation Technology of 1,1,2,3-Tetrachloropropene", Zhejiang Chemical Industry, vol. 41, No. 8 (2010).
International Search Report and Written Opinion, PCT/US2010/052107, mailed Jan. 12, 2011.

(Continued)

*Primary Examiner* — Sudhakar Katakam
(74) *Attorney, Agent, or Firm* — Lois K. Ruszala; KSJLaw, LLC

(57) ABSTRACT

The present invention provides continuous, gas phase, free radical processes for the production of chlorinated and/or fluorinated propenes or higher alkenes from the reaction of chlorinated and/or fluorinated alkanes and chlorinated and/or fluorinated alkenes, wherein wherein at least a portion of any intermediate boiler by-products generated by the process are removed from the process.

17 Claims, 2 Drawing Sheets

(56) References Cited

U.S. PATENT DOCUMENTS

| | | | |
|---|---|---|---|
| 5,895,825 A | 4/1999 | Elsheikh et al. | |
| 5,986,151 A | 11/1999 | Van der Puy et al. | |
| 6,111,150 A | 8/2000 | Sakyu et al. | |
| 6,118,018 A | 9/2000 | Savidakis | |
| 6,160,187 A | 12/2000 | Strickler et al. | |
| 6,187,976 B1 | 2/2001 | Van der Puy et al. | |
| 6,229,057 B1 | 5/2001 | Jackson et al. | |
| 6,472,573 B1 | 10/2002 | Yamamoto | |
| 6,545,176 B1 | 4/2003 | Tsay et al. | |
| 6,551,469 B1 | 4/2003 | Nair et al. | |
| 6,610,177 B2 | 8/2003 | Tsay et al. | |
| 6,825,383 B1 | 11/2004 | Dewkar et al. | |
| 6,958,135 B1 | 10/2005 | Filippi et al. | |
| 7,117,934 B2 | 10/2006 | Lomax et al. | |
| 7,189,884 B2 | 3/2007 | Mukhopadhyay et al. | |
| 7,226,567 B1 | 6/2007 | Olbert et al. | |
| 7,282,120 B2 | 10/2007 | Braun et al. | |
| 7,297,814 B2 | 11/2007 | Yada | |
| 7,345,209 B2 | 3/2008 | Mukhopadhyay et al. | |
| 7,371,904 B2 | 5/2008 | Ma et al. | |
| 7,378,559 B2 | 5/2008 | Verwijs | |
| 7,511,101 B2 | 3/2009 | Nguyen | |
| 7,521,029 B2 | 4/2009 | Guetlhuber | |
| 7,588,739 B2 | 9/2009 | Sugiyama | |
| 7,659,434 B2 | 2/2010 | Mukhopadhyay | |
| 7,674,939 B2 | 3/2010 | Mukhopadhyay | |
| 7,687,670 B2 | 3/2010 | Nappa | |
| 7,695,695 B2 | 4/2010 | Shin | |
| 7,714,177 B2 | 5/2010 | Mukhopadhyay | |
| 7,880,040 B2 | 2/2011 | Mukhopadhyay | |
| 7,951,982 B2 | 5/2011 | Mukhopadhyay | |
| 8,058,486 B2 | 11/2011 | Merkel et al. | |
| 8,058,490 B2 | 11/2011 | Strebelle | |
| 8,071,825 B2 | 12/2011 | Johnson | |
| 8,115,038 B2 | 2/2012 | Wilson | |
| 8,123,398 B2 | 2/2012 | Teshima et al. | |
| 8,158,836 B2 | 4/2012 | Pigamo et al. | |
| 8,232,435 B2 | 7/2012 | Sievert | |
| 2002/0110711 A1 | 8/2002 | Boneberg | |
| 2006/0150445 A1 | 7/2006 | Redding | |
| 2006/0258891 A1* | 11/2006 | Mukhopadhyay et al. | 570/172 |
| 2006/0292046 A1 | 12/2006 | Fruchey | |
| 2007/0112229 A1 | 5/2007 | Mukhopadhyay | |
| 2007/0197841 A1 | 8/2007 | Mukhopadhyay | |
| 2007/0197842 A1 | 8/2007 | Mukhopadhyay et al. | |
| 2007/0265368 A1 | 11/2007 | Rao et al. | |
| 2008/0021229 A1 | 1/2008 | Maughon et al. | |
| 2008/0118018 A1 | 5/2008 | Schrauwen | |
| 2008/0207962 A1 | 8/2008 | Rao | |
| 2009/0018377 A1 | 1/2009 | Boyce | |
| 2009/0030249 A1 | 1/2009 | Merkel | |
| 2009/0099396 A1 | 4/2009 | Mukhopadhyay | |
| 2009/0117014 A1 | 5/2009 | Carpenter | |
| 2009/0203945 A1 | 8/2009 | Mukhopadhyay | |
| 2009/0253946 A1 | 10/2009 | Van der Puy | |
| 2009/0306438 A1 | 12/2009 | Sievert | |
| 2010/0185029 A1 | 7/2010 | Elsheikh | |
| 2010/0210883 A1 | 8/2010 | Mukhopadhyay | |
| 2011/0083955 A1 | 4/2011 | Tirtowidjojo et al. | |
| 2011/0172472 A1 | 7/2011 | Sakyu | |
| 2011/0178343 A1 | 7/2011 | Tirtowidjojo | |
| 2011/0218369 A1 | 9/2011 | Elsheikh et al. | |
| 2011/0251442 A1 | 10/2011 | Okamoto | |
| 2012/0035402 A1 | 2/2012 | Wilson | |
| 2012/0041239 A1 | 2/2012 | Suzuki | |
| 2012/0065434 A1 | 3/2012 | Nose et al. | |

FOREIGN PATENT DOCUMENTS

| | | |
|---|---|---|
| CN | 101544535 | 9/2009 |
| CN | 101913979 | 12/2010 |
| CN | 101913980 | 12/2010 |
| CN | 101955414 | 1/2011 |
| CN | 101955414 A | 1/2011 |
| CN | 101982227 | 3/2011 |
| CN | 102001911 | 4/2011 |
| CN | 102249846 | 11/2011 |
| CN | 102351637 A | 2/2012 |
| DE | 857955 | 12/1952 |
| DE | 209184 | 4/1984 |
| DE | 235631 | 5/1986 |
| EP | 0131560 A1 | 1/1985 |
| EP | 0164798 | 12/1985 |
| EP | 1018366 | 12/2000 |
| EP | 1018366 A2 | 12/2000 |
| GB | 471188 | 8/1937 |
| GB | 857086 | 12/1960 |
| GB | 1134585 | 11/1968 |
| GB | 1381619 | 1/1975 |
| JP | 54-079207 A | 6/1979 |
| JP | 2001151708 | 6/2001 |
| JP | 2001213820 | 8/2001 |
| JP | 2007021396 | 2/2007 |
| JP | 2007021396 A | 2/2007 |
| JP | 2008063314 | 3/2008 |
| JP | 2009046653 | 3/2009 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2007079431 | 7/2007 |
| WO | 2007079435 | 7/2007 |
| WO | 2009003084 A1 | 12/2008 |
| WO | 2009067571 | 5/2009 |
| WO | 2009087423 | 7/2009 |
| WO | 2011060211 | 5/2011 |
| WO | 2011065574 | 6/2011 |
| WO | 2012166393 | 12/2012 |

OTHER PUBLICATIONS

Boualy et al., "Kharasch addition of Tetrachloromethane to alkenes catalyzed by metal acetylacetonates", Catalysis Communications, 2011, 1295-1297, 12.
Cristiano et al., Tetraalkylphosphonium Trihalides. Room Temperature Ionic Liquids As Halogenation Reagents, J. Org. Chem., 2009, 9027-9033, 74.
Evstigneev et al., "Initiated Chlorination of Tetrachloropropane", Khim. Prom., 1984, 393-394,16:7.
Ivanov et al., "Metal phthalocyanine-catalyzed addition of polychlorine-containing organic compounds to C=C bonds," Russian Chemical Bulletin, International Edition, 2009, 2393-2396 58(11).
Kharasch et al., "Chlorinations with Sulfuryl Chloride.I. The Peroxide-Catalyzed Chlorination of Hydrocarbons", J. Am. Chem. Soc., 1939, 2142-2150, 61.
Munoz-Molina et al., "An Efficient, Selective and Reducing Agent-Free Copper Catalyst for the Atom-Transfer Radical Addition of Halo Compounds to Activated Olefins", Inorg. Chem., 2010, 643-645, 49.
Nair et al., "Atom transfer radical addition (ATRA) of carbon tetrachloride and chlorinated esters to various olefins catalyzed by CP/Ru(PPh3)(PR3)Cl complexes", Inorganica Chimica Acta, 2012, 96-103, 380.
Rotshtein et al., "Isomer Distribution on Chlorination of Chloropropanes", Z. Organicheskoi Khimii, 1966, 1539-1542, 2(9).
Semenov et al., "Selectivity of Photochemical Chlorination of Chloromethane in the Liquid Phase", Viniti, 1988, 3405-84.
Tanuma et al., "Partially Fluorinated Metal Oxide Catalysts for a Friedel-Crafts-type Reaction of Dichlorofluoromethane with Tetrafluoroethylene", Catal. Lett., 2010, 77-82, 136.
Ying et al., Isomerization of tetrachloropropene to promote utilization ration of triallate raw materials, Petrochemical Technology & Application, 2007, 25(1).
Herzfelder, "Substitution in the Aliphatic Series", Berichte der Deutschen Chemischen Gesellschaft, 1893, 1257-1261, 26(II).
McBee et al., "Utilization of Polychloropropanes and Hexachloroethane", Industrial and Engineering Chemistry, Feb. 1941, 176-181, 33(2).
Mouneyrat, "Effect of chlorine on propyl chloride in the presence of anhydrous aluminum chloride", Bulletin de la Societe Chimique de Paris, Jan. 1899, 616-623, 3(21).

(56) References Cited

OTHER PUBLICATIONS

Chai et al., "Study of Preparation of 1,1,1,3-Tetrachloropane", Zhejiang Chemical Industry, 2010, pp. 1-3, 41(5).

Gault et al., "Sur la chloruatoin du chloroforme", Comptes Rendus Hebdomadaires des seances de L'Academie de Sciences, 1924, pp. 467-469, 179.

Gerding et al., "Raman Spectra of Aliphatic Chlorine Compounds II. Chloroethanes and chloropropanes", Recueil des travaux chimiques des pays bas, 1955, pp. 957-997.

Hatch et al., "Allylic Chlorides. XV. Preparation and Properties of the 1,2,3-Trichlooropropenes", JACS, Jan. 5, 1952, pp. 123-126, 74(1).

Hatch et al., "Allylic Chlorides. XVIII. Preparation and Properties of 1,1,3-Tricloro-2fluoro-1-propene and 1,1,2,3-Tetrachloro-1-propene", JACS, Jul. 5, 1952, pp. 3328-3330, 74(13).

Kang et al., "Kinetics of Synthesis of 1,1,1,3,3,-pentachlorobutane catalyzed by Fe—FeCl3", Huaue Yanjiu Yu, Yingyong, 2011, pp. 657-660, 23(6).

Khusnutdinov et al., "Addition of CCl4 to olefins catalyzed by complexes of chromium and ruthenium. Effect of water as a nucleophilic additive," Neftekhimiha, 2009, pp. 349-356, 49(4).

Leitch, "Organic Deuterium Compounds: V. The Chlorination of Propyne and Propyne-d4", Canadian Journal of Chemistry, Apr. 1, 1953, pp. 385-386, 31(4).

Levanova et al., "Thermocatalytic Reactions of Bromochloropropanes", Russian Journal of Physical Chemistry, Chemical Society, London, GB, Jan. 1, 1983, pp. 1142-1146 vol. 57.

Liu et al., "Progress in Synthesis of 1,1,1,3-tetrachloropropane", Guangzhou Huabonb (2011), pp. 41-42, 39(5).

Pozdnev et al., "Chlorination of Chloroform and the conversion of methylene chloride manufacture still residues", Khim. Khim. Tekhnol., 1970, pp. 70-74, 70(4).

Skell et al., "Selectivities of pi and sigma Succinimidyl Radicals in Substitution and Addition Reactions. Appendix: Response to Walling, El-Taliawi and Zhao", JACS, 1983, pp. 5125-5131, 105(1).

Skell et al., "Reactions of BrCl with Alkyl Radicals", Tetrahedron Letters, 1986, pp. 5181-5184, 27(43).

Urry et al., Free-Radical Reactions of Diazomethanewith Reactive Bromopolychloroakanes, JACS, May 5, 1964, pp. 1815-1819, 86(9).

Wang, "Elimination Reactions of Polyhalopropanes under Emulsion Catalytic Conditions to give Halopropenes", Synthesis, Georg Thieme Verlag, Stuttgart, DE, Jan. 1, 1982, pp. 494-496, 1982(6).

Zheng et al., "Preparation of the low GWP alternative 1,3,3,3-tetrafluoropropene", Zhejiang Huagong, 2010, pp. 5-7, 41(3).

\* cited by examiner

PROCESSES FOR THE PRODUCTION OF CHLORINATED AND/OR FLUORINATED PROPENES AND HIGHER ALKENES

FIELD

The present invention relates to continuous, gas phase, free radical processes for the production of chlorinated and/or fluorinated propene and higher alkenes, wherein the efficiency of the process is enhanced.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser detrimental impact on the ozone layer and their generally lower GWP. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene (HFO-1234yf) or 1,3,3,3-tetrafluoroprop-1-ene (HFO-1234ze), may typically be produced utilizing feedstocks of chlorinated propenes.

Unfortunately, these chlorinated propenes have limited commercial availability, and/or may only be available at potentially prohibitively high cost. These barriers to commerciality are due at least in part to challenges inherent in conventional processes for the manufacture of chlorinated and/or fluorinated propenes, and yet unique relative to gas-phase, free radical halogenations reactions. Because of the unique chemistry involved in the production of halogenated propenes or higher alkenes, solutions expected to be useful for challenges encountered in conventional gas phase, free radical halogenations reactions may not be applicable to these processes.

It would thus be desirable to provide improved processes for the production of chlorinated and/or fluorinated propenes and higher alkenes, such as those that may be useful in the synthesis of HFO's. More particularly, such processes would provide an improvement over the current state of the art if they were less costly not only in materials, but in time expenditure.

BRIEF DESCRIPTION

The present invention provides improved processes for the production of chlorinated and/or fluorinated propenes or higher alkenes wherein the processes exhibit an enhanced efficiency as compared to conventional processes. More specifically, the processes provide for the removal of intermediate boiler by-products from the process, so that process capacity is maintained and reactor fouling, or the impact of the same, may be reduced. And so, time and cost savings are provided in that the desired throughput of the reactor may be substantially maintained for a longer period of time than if the intermediate boiler by-products were not removed. Further, in some embodiments, the present processes make use of the intermediate boiling, or other, by-products by purifying them for use in other processes or sale. Reaction components, including other by-products, may also be recycled, if desired, thereby adding further cost savings to the present processes.

In one aspect of the present invention then, there is provided a continuous, gas phase, free radical process for the production of chlorinated and/or fluorinated propenes or higher alkenes. The process comprises removing at least a portion of any intermediate boiler by-products that may be generated by the process, from the process. In some embodiments, the efficiency of the process is further enhanced by one or more of i) reducing fouling within the process and/or minimizing the impact of any fouling that may occur, ii) recycling at least a portion of any unreacted reactants, products, other by-products and/or diluents, and/or iii) purification of at least one product and/or byproduct of the reaction. Combinations of two or all three of these can be utilized, in which case the advantages of one may at least be additively, if not synergistically, leveraged.

The processes described herein are expected to provide particular benefit when utilized to produce chlorinated and/or fluorinated propenes or higher alkenes, and in another aspect, the present invention so provides. Particular chlorinated and/or fluorinated propenes or higher alkenes advantageously produced utilizing the present process include, for example, 1,1,2,3-tetrachloropropene, 1,1,3,3-tetrachloropropene, 1,1,2,3-tetrafluoropropene and 1,1,2-trichloro-3-fluoropropene. The advantages provided by the present processes may be carried forward by utilizing the chlorinated and/or fluorinated propenes or higher alkenes to produce further downstream products, such as, e.g., 2,3,3,3-tetrafluoroprop-1-ene (HFO-1234yf) or 1,3,3,3-tetrafluoroprop-1-ene (HFO-1234ze).

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

Figure 1:
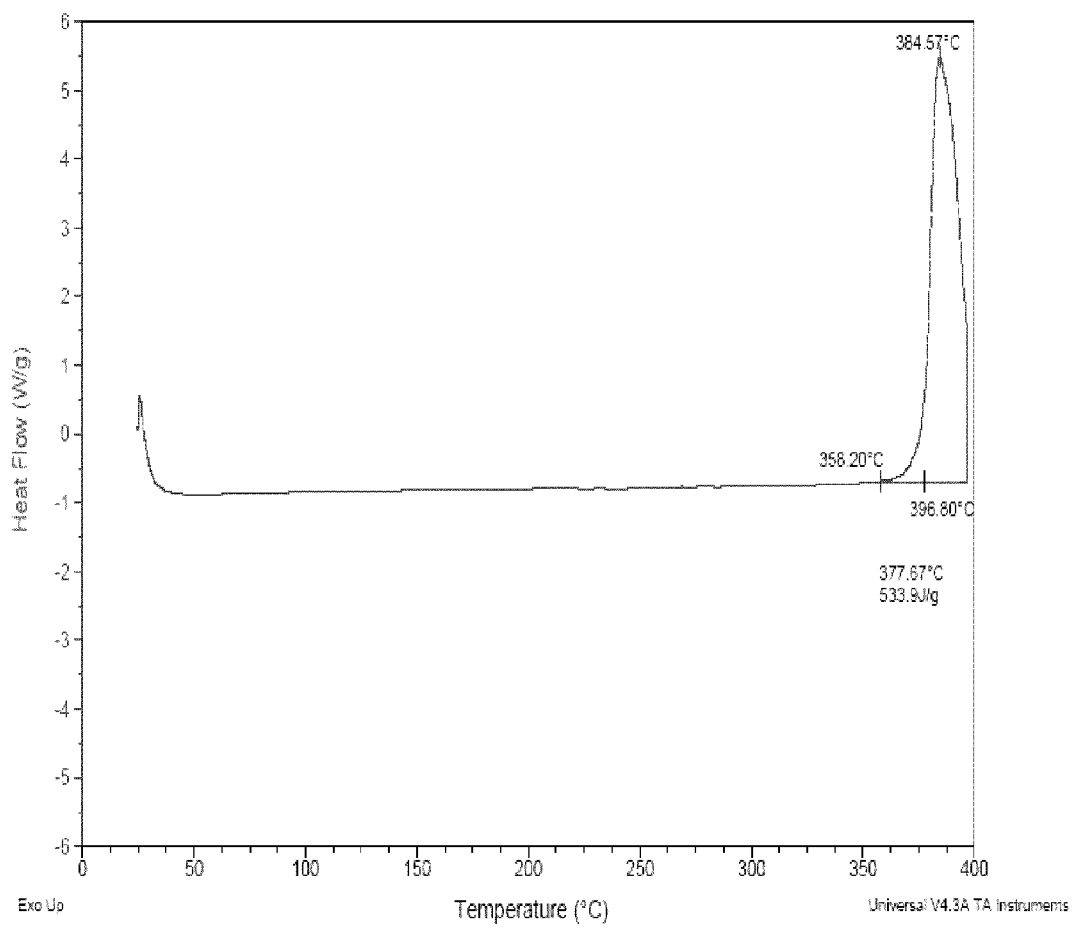
FIG. 1 is a graphical depiction of the results of the Differential Scanning calorimetry (DSC) analysis of 1,1,2,3-tetrachloropropene.

The present specification provides certain definitions and methods to better define the present invention and to guide those of ordinary skill in the art in the practice of the present invention. Provision, or lack of the provision, of a definition for a particular term or phrase is not meant to belie any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Throughout this specification, and in efforts to provide particular examples of the concepts taught herein, reference may occasionally be made to the reaction of methyl chloride with perchloroethylene to provide 1,1,2,3-tetrachloropropene, the reaction of methyl fluoride with perchloroethylene to provide 1,1,2-chloro-3-fluoro-propene, or reactions of methanes, including chloromethanes, fluoromethanes or chlorofluoromethanes having the formula $CH_{4-a-b}Cl_aF_b$, wherein each a and b are independently 0-3 and 4-a-b is greater than 0, and chloroethylenes or chlorofluoroethylenes comprising at least one chlorine atom to provide compounds according to the formula $CH_{2-c-g}Cl_cF_g=CH_{1-d-h}Cl_dF_h-CH_{3-e-f}Cl_eF_f$ wherein c is 0-2, d is 0-1, e is 0-3, f is 0-3, and g is 0-2 while c+g≤2, d+h≤1, and e+f≤3. However, these references are intended only to be exemplary and are not to be construed as limiting to the reactors and concepts described herein.

The present invention provides improved processes for the production of chlorinated and/or fluorinated propenes or higher alkenes. Preferred alkenes produced by the present process include those having from about three to about six carbon atoms. Particular exemplary reactions include the reaction of methyl chloride with perchloroethylene to provide 1,1,2,3-tetrachloropropene, methylene chloride and trichloroethylene to provide 1,1,3,3-tetrachloropropylene, methyl fluoride with chlorotrifluoroethylene to provide 1,1,2,3-tetrafluoropropylene, and methyl fluoride with perchloroethylene to provide 1,1,2-chloro-3-fluoro-propene. However, these reactions are only exemplary and are not to be construed as limiting to the concepts described herein.

Unlike conventional halogenations reactions, i.e., those in which a halogen providing compound is the limiting reagent and experiences 100% conversion, such as the thermal chlorination of propylene to produce allyl chloride, processes for the production of chlorinated and/or fluorinated propenes and higher alkenes may have one or more limiting reactants that exhibit a mass or molar conversion of 80%, or less than 40%, or even less than 20% of the limiting reactant. Because of this difference, among others, the challenges expected to be encountered in the conventional gas-phase, free radical halogenations reactions may not typically be encountered in the gas-phase free radical chlorination or fluorination of propenes or higher alkenes, and vice versa. Solutions expected to be useful in one process are therefore not necessarily expected to be useful in the other.

For example, processes for the production of chlorinated or fluorinated propenes may typically result in the formation of larger quantities of reaction by-products than conventional halogenation processes that may not experience the formation of appreciable quantities of, if any, by-products. That is, in conventional free-radical halogenations reactions, reactor promoted backmixing or recirculation, such as that provided by jet-stirred reactors, is typically considered to increase productivity of the process, without concurrent increases in by-product formation. [Liu et al., *Chemical Engineering Science*, 59, (2004) 5167-5176]. In the present processes, such backmixing or recirculation can result in the formation of unacceptable amounts of by-products.

The formation of large quantities of by-products, in turn, can not only detrimentally impact process capacity and conversion, but can be problematic for other reasons as well, not the least of which being that the same can cause reactor fouling. Reactor fouling can effectively reduce the reactor volume available for the desired reaction to take place. Undesirable time or cost expense may also be added to the process, via the cleaning necessitated for a reactor fouled to such an extent that a commercially acceptable throughput is no longer possible.

The present improved processes for the production of chlorinated and/or fluorinated propenes or higher alkenes thus provide for the removal of at least a portion of certain by-products produced by, or otherwise introduced into, the process. More specifically, it has also now been discovered that although certain by-products may advantageously be recycled back to the reactor, where they may be expected to minimize fouling and also enhance reaction rates and thus improve reactor capacity, others could accumulate in the system and can significantly and quickly reduce the process capacity and thus render the process uneconomical. On the other hand, it has also been discovered that some byproducts with boiling points in between of the two reactants being recycled back will desirably be purged or removed from the process to maintain the process capacity. Otherwise, these intermediate boiler byproducts (IBBs), even though formed in quantities as low as less than 0.1 wt % of the reactor effluent, could accumulate in the system and can significantly and quickly reduce the process capacity and thus render the process uneconomical.

For example, in the exemplary reaction of methyl chloride and perchloroethylene to produce 1,1,2,3-tetrachloropropylene, by-products may include hydrogen chloride, methylene chloride, chloroform, tetrachlorobutenes, hexachloroethane, hexachloropropene and heavier by-products. The byproducts hexachloroethane and hexachloropropene, may be recycled to the reactor, where they would be expected to improve reactor capacity by enhancing reaction kinetics. Hydrogen chloride can also be used as a diluent to minimize fouling in the reactor zone and in any evaporators used since hydrogen chloride can lower the evaporator temperature. On the other hand, methylene chloride and chloroform, with their boiling points of 39.8° C. and 61° C. respectively, represent intermediate boiler byproducts with respect to the reactants methyl chloride and perchloroethylene, which have boiling points of −24.2° C. and 121° C., respectively. Although methylene chloride and chloroform are formed in a small quantity of less than 0.1 wt % in the reactor effluent as a result of methyl chloride side reaction with initiators, they will accumulate in the process in the reactant recycle streams. In the present processes, at least a portion of the methylene chloride and/or chloroform produced by, or introduced into, the process would be removed.

The desired intermediate boiler byproducts may be removed from the present processes in any amount expected to provide an improvement in process capacity, although even small amounts are expected to be beneficial. Of course, the particular amount to be removed will depend on the particular process being carried out. Generally speaking then, and with respect to that embodiment of the process wherein methyl chloride and perchloroethylene are reacted to produce 1,1,2, 3-tetrachloropropylene, methylene chloride and/or chloroform, may be recycled in amounts of up to about 0.5 or 1 or 2 or even 5 mole % of the feed stream to the reactor.

The intermediate boiling by-products may be removed by any suitable method known to those of ordinary skill in the art. Suitable methods include, but are not limited to, distillation, filtration, purging a fraction of the reactant recycle streams sufficient to prevent accumulation of the byproducts in the system, adsorption into an active carbon bed, cyclone separator, centrifuge, sedimentation, or combinations of these. In preferred embodiments, at least a portion of any such intermediate boiling by-products are desirably removed from the process via purging a fraction of reactant recycle streams and/or utilization of a dividing wall column.

If purging is desirably employed to remove at least a portion of any intermediate boiling by-products, intermediate boiler byproducts may be purged in a reactant recycle column as a side draw from the column. Or, a purge may be taken of a reactant recycle stream to keep the intermediate boiler by-products from accumulating in the reactor. For either purge method, the purge rate should be sufficient to minimize the impact of the intermediate boiler by-products on the productivity of the reactor.

Dividing wall columns are well known to those of ordinary skill in the chemical engineering art, and provide the advantage that any intermediate boiling by-products removed can be separated or purified in a single column instead of employing two or more columns. Dividing wall columns, and the use thereof in manufacturing processes, are described in "Dividing Wall Columns Find Greater Appeal", by Gerald Parkinson, Chemical Engineering Progress, May 2007, hereby incorporated herein by reference in its entirety for any and all purposes.

For the exemplary reaction of methyl chloride and perchloroethylene to produce 1,1,2,3-tetrachloropropene, a dividing wall column may be utilized to remove methyl chloride, methylene chloride and chloroform, by providing reactor effluent having had a majority of any hydrogen chloride and lighter boilers than methyl chloride removed therefrom via distillation to the dividing wall column. The dividing wall column would be expected to separate the effluent into methyl chloride, recovered from an upper portion of the column; methylene chloride and chloroform, recovered from a middle portion of the column, and unreacted perchloroethylene and 1,1,2,3-tetrachloropropene, and other heavies or high boilers from a bottom portion of the column.

Appropriate operating conditions of a dividing wall column will depend on the separation desirably being conducted therein, and those of ordinary skill in the art of chemical engineering are readily able to determine the same. For the exemplary reaction of methyl chloride and perchloroethylene to provide 1,1,2,3-tetrachloropropene, wherein methyl chloride, methylene chloride, chloroform, perchloroethylene, and 1,1,2,3-tetrachloropropene are desirably separated, suitable operating conditions for the dividing wall column include a pressure of about 266 psia and temperature of about 91° C. at the feed stream, a pressure of about 63 psia and a temperature of about 16° C. at the overhead, and a pressure of about 68 psia and a temperature of about 186° C. at the column bottom.

In addition to removing at least a portion of any by-products from the process, the present processes can achieve a conversion within a desired range, by reducing the by-products produced, or the impact of any by-products produced. For example, in some embodiments, the conversion can be caused to increase less than about 5%, or less than about 2%, or even less than about 1%, so that a desired selectivity can be seen. Stated another way, at a limiting reagent conversion of at least about 5%, or at least about 10%, or at least about 15%, or even at least about 20%, selectivity to the desired product can be as high as about 70%, or about 75%, or about 80%, or even about 85% or greater.

In some embodiments, this can be accomplished by protecting any thermally sensitive components utilized in the process, e.g., reactants, products, catalysts, or even by-products, so that substantial detrimental reaction or degradation of the same does not occur. The present processes provide further efficiencies by recycling one or more of the reaction components, i.e., diluents, reactants, products, by-products (other than the intermediate boiling by-products, or up to about 2 wt % of the intermediate boiling by-products) and/or initiators, so that cost savings are provided. In some embodiments, the recycled components can be purified to reduce or eliminate the impact of any contaminants therein on the present process, or in downstream processes in which the components may be used. Cost and time savings may also be provided by avoiding process shut-downs that may be necessitated by excessive reactor fouling.

More particularly, the present continuous, gas phase, free radical processes for the production of chlorinated and/or fluorinated propenes or higher alkenes can provide enhanced efficiency, by one or more of i) reducing fouling within the process and/or minimizing the impact of any fouling that may occur, ii) recycling at least a portion of any reaction component, i.e., unreacted reactants, diluents, products, by-products and/or initiators, and/or iii) purification of at least one product and/or byproduct of the reaction.

The present process provides a variety of methodologies for reducing fouling therein, or, minimizing the impact of any fouling that may otherwise occur. In one embodiment, for example, the present process can provide minimized fouling within the process by incorporating a diluent therein. Desirably, any diluent(s) utilized in the process with be capable of absorbing at least a portion of the heat of reaction generated, thereby assisting in the maintenance of the desired temperature within the reactor. By maintaining the desired temperature, a reduction in the production of by-products can be seen, either by minimizing reactions that may produce the same, or in preventing the decomposition of any thermally sensitive components that may occur at higher temperatures to produce such by-products.

Suitable diluents will thus include those that have a boiling point lower than i) a desired reaction temperature, ii) a temperature at which substantial by-products will form and/or iii) a temperature at which any thermally sensitive component utilized in the process will degrade. Because suitable diluents(s) will have a boiling point lower than at least one, or many, component(s) utilized or generated by the process, it/they may advantageously be readily and easily separated from a reactor effluent. And, suitable diluents will desirably substantially inert within the process, i.e., will not react with any of the reaction components or otherwise substantially interfere with the reaction(s) desirably taking place. Taking these considerations into account, suitable diluents include, but are not limited to hydrogen chloride, nitrogen, argon, helium, krypton, or combinations of these. In those embodiments of the invention wherein methyl chloride is reacted with perchloroethylene to provide 1,1,2,3-tetrachloropropene, the use of hydrogen chloride can be preferred as it is a byproduct of the reaction.

The desired diluents can be added to the process at any point, and will desirably be added so that the heat absorption characteristics thereof can be taken full advantage of, i.e., at least prior to the reaction zone. Typically such diluents may be added at the same point as the other reactant feeds, i.e., at a reactor inlet and/or mixer fluidly connected to a reactor inlet, and in such embodiments, is expected to lower the evaporation temperature of the same. Further, any suitable diluent(s) utilized may either be provided as a separate feed, i.e., through a separate inlet, comprising separate temperature and flow controls, or may be provided in combination with one or more reactant feeds, or recycled reactant feeds, wherein the temperature and flow controls are also combined with those for the reactant feed(s).

Of course, the particular process parameters at which the desired diluents are employed within the process will depend on the diluent(s) selected, and the process in which it is desirably used, and those of ordinary skill in the chemical engineering art are capable of determining the same. In the exemplary reaction of methyl chloride and perchloroethylene to produce 1,1,2,3-tetrachloropropene, hydrogen chloride may be added to the process at a temperature of from about 200° C. to about 500° C. and at a mole % of the feed to the reactor from about 5% to about 30%. In such reactions, the HCl may be added in combination with the feed of either methyl chloride or perchloroethylene, if desired.

The impact of any fouling that may occur within the process may also be minimized in some embodiments of the present processes by removing any intermediates, contaminants and/or by-products that may be formed from the process in addition to the intermediate boiling by-products. In embodiments where the same is desired, the intermediates, contaminants and/or by-products may be removed by any suitable method known to those of ordinary skill in the art. Suitable methods include, but are not limited to, distillation, filtration, purging a fraction of the reactant recycle streams sufficient to prevent accumulation of the byproducts in the system, adsorption into an active carbon bed, cyclone separator, centrifuge, sedimentation, or combinations of these. In preferred embodiments, at least a portion of any such intermediates, contaminants and/or by-products are desirably removed from the process via filtration, utilization of a dividing wall column as described above.

If filtration is desirably employed, appropriate filters may be provided at any point in the process wherein at least a portion of any solid impurities desirably removed are flowing therethrough. For example, filters that can exclude 1 micron size particles, or larger, could be placed in the process stream at any point within the process, e.g., prior to entry into the reactor, or after exit therefrom, and prior to entering any further processing equipment, such as distillation columns or reboilers, for example. Such filters are expected to be effective to remove at least a portion of any solid by-products and carbonaceous particles produced within the process.

Fluid intermediates, contaminants and/or by-products within the exemplary process may also be removed via incorporation of a dividing wall column within the process. In such embodiments, the dividing wall column may be operatively disposed relative to the reactor to receive, e.g., reactor effluent, and may be expected to provide separated fractions of low boilers from an upper portion of the column, midboilers from the middle of the column, and higher boiling by-products from the bottom of the column.

In some embodiments, any such impurities removed from the process may be subject to one or more purification methods so that the same can be sold, made use of in other manufacturing processes, or recycled to the reactor. Such embodiments recognize that impurities in one process may be useful in another, and provide cost savings and other efficiencies by processing such impurities so as to be in a useful state therefore.

Although the above methods of reducing fouling within the process are expected to be very effective, in other embodiments of the present processes, methods of reducing the impact of any fouling that may nonetheless occur are provided. For example, the impact of any fouling that may occur in the process can be reduced, and desirably eliminated by operating the process with two or more reactors. In such embodiments, should any fouling occur, the fouled reactor may be shut down and cleaned without shutting down the process entirely.

If those embodiments wherein the same is desired, a second reactor would be positioned to be in parallel flow with the first reactor and will desirably be started up before the first reactor is shutdown, thus allowing uninterrupted operation. Similarly, a process can contain three or more reactors that can be operated two at a time to meet production demand using milder (lower temperature) conditions to minimize fouling. The two reactors will desirably be brought online at different times, so that any fouling that occurs is to a different degree in each reactor. If fouling occurs that interferes with production, the third reactor can be brought online before the fouled reactor is shut down for cleaning.

In other embodiments, the efficiency of the present processes may be enhanced by recycling at least a portion of any reaction component, i.e., unreacted reactants, diluents, products, initiators and/or by-products (other than the intermediate boiling by-products, or up to about 2 wt % of the intermediate boiling by-products). Cost savings are thus provided to the present processes. If so desired, the reactants, diluents, products, by-products and/or initiators may be recycled back to the reactor, may be recycled for use in other downstream or unrelated processes, or, may even be recycled for sale as finished products.

The recycled reactants, diluents, products, by-products and/or initiators may be purified, if desired, prior to recycling. In embodiments where the same is desired, any suitable purification method may be utilized, and the choice of the same will depend on what is being purified, and may be readily determined by those of ordinary skill in the art. Exemplary suitable methods of purification may include, but are not limited to, the use of a cryogenic tower. Cryogenic towers are known to those of ordinary skill in the art and generally speaking comprise a multistage distillation column that utilizes low temperature to remove low boiling point products or byproducts. Such towers and the use thereof are described in U.S. Pat. No. 5,372,009, hereby incorporated by reference herein for any and all purposes, to the extent the teachings therein do not contradict the present teachings.

In the exemplary reaction of methyl chloride and perchloroethylene to produce 1,1,2,3-tetrachloroethylene, a cryogenic tower may be utilized, and provided with trays with sufficient stages to remove the diluent hydrogen chloride and unreacted methyl chloride, e.g., at a temperature of about $-14°$ C. and a pressure of about 259 psia at the overhead and a temperature of about 91° C. and a pressure of about 266 psia at the bottom of the tower, when the feed is provided at a temperature of about 50° C. and at a pressure of about 267 psia. Unreacted perchloroethylene can be separated and recycled, if desired, using a column with tray or packing with, for example, at least 54 theoretical stages or using 76 trays assuming 70% of tray efficiency. Such a column would be expected to provide about 95 wt % of Perc and 5 wt % of carbon tetrachloride at the overhead at a temperature of about 117° C. and a pressure of about 15 psia, while the bottom is set at temperature of about 192° C. and a pressure of about 26 psia.

As mentioned above, the present processes may be used to produce any chlorinated and/or fluorinated alkenes. Preferred alkenes have from three to about six carbon atoms. Chlorinated and/or fluorinated propenes, in particular, may advantageously be produced by the present continuous process, and particular, but non-limiting, examples of these include the reaction of methyl chloride with perchloroethylene to provide 1,1,2,3-tetrachloropropene, the reaction of methyl fluoride with perchloroethylene to provide 1,1,2-chloro-3-fluoro-propene, the reaction of methylene chloride and trichloroethylene to provide 1,1,3,3-tetrachloropropylene, and the reaction of methyl fluoride with chlorotrifluoroethylene to provide 1,1,2,3-tetrafluoropropylene.

In such embodiments, the advantages provided herein can be further leveraged by utilizing a process reaction temperature of less than 500° C., or less than about 450° C., or less than about 400° C., or less than about 350° C. or even lower. Conventional processes for the production of 1,1,2,3-tetrachloropropene are typically carried out at higher temperatures, which not only provides a cost disadvantage when compared to the present processes, but can also result in increased production of by-products and/or reactor fouling, and thus suffer from lowered selectivity and process yield. That is, 1,1,2,3-tetrachloropropene itself is not only thermally unstable, but also, prone to react further with reactants and/or other byproduct(s) to form yet other by-products.

More particularly, 1,1,2,3-tetrachloropropene is very reactive at 370° C. with methyl chloride and perchloroethylene, thermally unstable at 400° C.-500° C., and especially unstable at conventional reaction conditions of from about 500° C. to about 750° C. The ensuing undesired reactions and/or decomposition leads to high concentrations of impurities, and ultimately thermal coking at these higher temperatures. For continuously fed, industrial reactors, coking is well known to cause further loss of reactor production capacity with time and often requires shutting down a reactor for cleaning and maintenance. Although the present invention is not so limited, reactions to produce 1,1,2,3-tetrachloropropene, as well as other similar reactions comprising reactants, products, diluents or byproducts with similar thermal sensitivity, are examples of those that can find particular benefit from application of the principles disclosed herein.

To further leverage the advantages provided by the lower operating temperatures, in some embodiments, higher pressure, i.e., greater than ambient, may be also be utilized in the exemplary reaction for the production of 1,1,2,3-tetrachloropropene. One particular such embodiment may utilize a reaction pressure of at least about 200 psig, or about 300 psig, or about 400 psig, a reaction temperature of lower than about 500° C., or lower than about 450° C., or even lower than about 400° C., or even lower than about 350° C. A catalyst/initiator, e.g., such as those comprising chlorine, including but not limited to, chlorine gas, carbon tetrachloride, or hexachloroethane or combinations of these, in a concentration of from about 5 ppm to about 100000 ppm, or from about 10 ppm to about 50000 ppm, or from about 20 ppm to about 10000 ppm, depending on the particular initiator utilized.

The present processes may be conducted in any suitable reactor. Desirably, the reactor utilized will be one wherein the reaction conditions are readily and easily altered as desired. These are expected to include near-isothermal shells and multitube reactors where the desired temperature can be achieved by means of utilization of a heat transfer fluid. Adiabatic and/or adiabatic plug flow using cylindrical or tube reactors may also be used, and if used can have any desired length to diameter aspect ratio so long as preheating to the desired reaction temperature is possible. Alternatively, a series of adiabatic reactors with at least one intercooler operatively disposed relative thereto can also be employed to obtain the desired overall conversion while maintaining the desired temperature rise within each reactor.

The efficiencies provided by the present processes can be further leveraged by providing the chlorinated and/or fluorinated propenes or higher alkenes produced therein to further downstream processes. For example, 1,1,2,3-tetrachloropropene or 1,1,2-chloro-3-fluoro-propene produced by the present process can be processed to provide further downstream products including hydrofluoroolefins, such as, for example, 2,3,3,3-tetrafluoroprop-1-ene (HFO-1234yf) or 1,3,3,3-tetrafluoroprop-1-ene (HFO-1234ze). Improved processes for the production of hydrofluoroolefins, 2,3,3,3-tetrafluoroprop-1-ene (HFO-1234yf) or 1,3,3,3-tetrafluoroprop-1-ene (HFO-1234ze), are thus also provided herein.

The conversion of chlorinated and/or fluorinated propenes or higher alkenes to provide hydrofluoroolefins may broadly comprise a single reaction or two or more reactions involving fluorination of a compound of the formula $C(X)_m CCl(Y)_n (C)(X)_m$ to at least one compound of the formula $CF_3 CF=CHZ$, where each X, Y and Z is independently H, F, Cl, I or Br, and each m is independently 1, 2 or 3 and n is 0 or 1. A more specific example might involve a multi-step process wherein a feedstock of 1,1,2,3 tetrachloropropene is fluorinated in a catalyzed, gas phase reaction to form a compound such as 2-chloro-3,3,3-tri-fluoropropene. The 2-chloro-2,3,3,3-tetrafluoropropane is then dehydrochlorinated to 2,3,3,3-tetrafluoropropene via a catalyzed, gas phase reaction.

The following examples are set forth for the purpose of illustrating the invention; but these examples are not intended to limit the invention in any manner. One skilled in the art will recognize a variety of substitutions and modifications of the examples that will fall within the scope of the invention. Particularly, even though the present description and examples refer with specificity to the reaction of methyl chloride with perchloroethylene, the teachings herein, and advantages provided thereby, are expected to be readily and easily extrapolated by those of ordinary skill in the art to any free radical type reaction desirably conducted in the gas phase, and desirably employing chlorine radical catalyst/initiators.

EXAMPLE 1

Reaction of Two Chlorinated and/or Fluorinated Alkanes and Chlorinated and/or Fluorinated Alkenes having the Formula $CH_{4-a-b}Cl_a F_b$ to Produce a Chlorinated and/or Fluorinated Propene According to the Formula $CH_{2-c-g}Cl_c F_g=CH_{1-d-h}Cl_d F_h-CH_{3-e-f}Cl_e F_f$ An empty Hasteloy tube of 10 inch length and 1 inch diameter is used to run the reaction. Constant flows of two chlorinated and/or fluorinated alkanes and chlorinated and/or fluorinated alkenes having the formula $CH_{4-a-b}Cl_a F_b$, wherein a and b are each independently 0-3 and 4-a-b is at least one and carbon tetrachloride flow is provided to, and maintained in, the reactor whereas flows of the by-products are varied to obtain desired mole percent of flow to the reactor.

Reaction temperature is obtained by externally heating the reactor tube. The feed is typically preheated to 325° C. and reactor temperature can be varied between 400° C. to 430° C. The impact of the presence of the by-products on $CH_{4-a-b}Cl_aF_b$ conversion is investigated at a fixed temperature and residence time.

EXAMPLE 2

Figure 2:
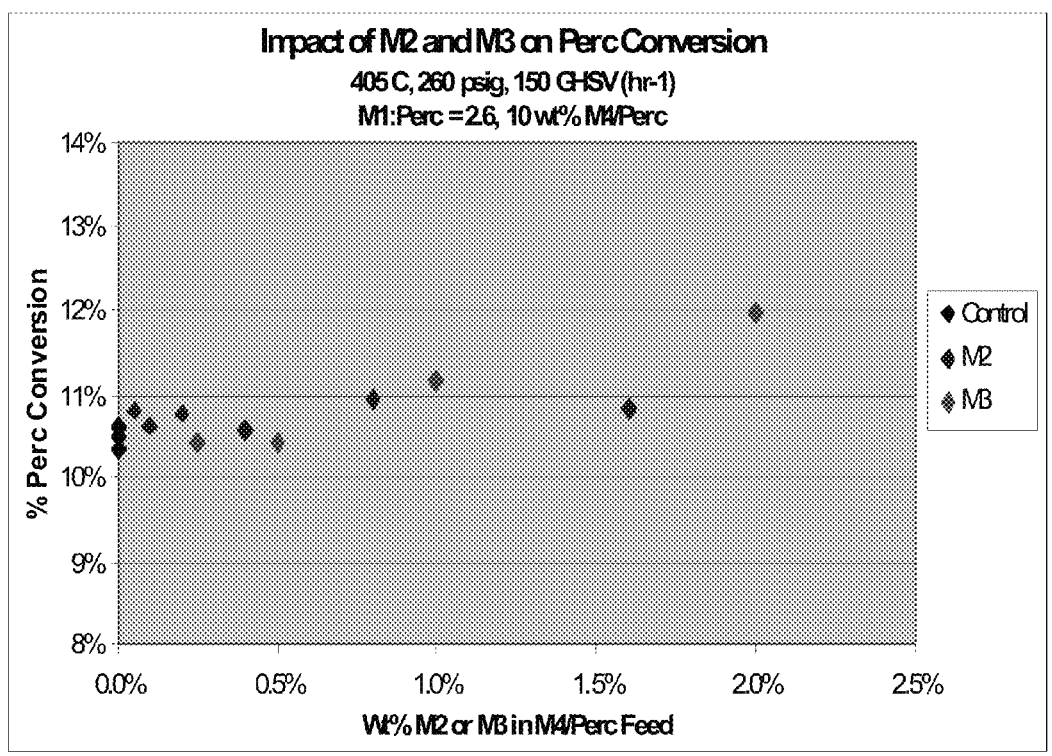
FIG. 2 is a graphical depiction of the impact of HCl, methylene chloride and chloroform on perchloroethylene conversion at a fixed temperature.

Reaction of the Chlorinated and/or Fluorinated Alkanes and Chlorinated and/or Fluorinated Alkenes Methyl Chloride and Perchloroethylene to Produce the Chlorinated and/or Fluorinated Propene 1,1,2,3-tetrachloropropene An empty Hasteloy tube of 10 inch length and 1 inch diameter is used to run the reaction. Constant methyl chloride, perchloroethylene and carbon tetrachloride flow is provided to, and maintained in, the reactor whereas flows of the by-products hydrogen chloride, methylene chloride, and chloroform are varied. More specifically, the flow of HCl is varied from 0 mole % to 20 mole % methylene chloride is varied from 0 mole % to 1.2 mole % and chloroform is varied from 0 to 0.8 mole % in the feed stream to the reactor Reaction temperature is obtained by externally heating the reactor tube. The feed is typically preheated to 325° C. and reactor temperature can be varied between 400° C. to 430° C. The impact of the presence of the by-products hydrogen chloride, methylene chloride and chloroform on perchloroethylene conversion is investigated at a fixed temperature and residence time. The data obtained in this example is shown in FIG. 2.

HCl was found to have no impact on improving reactor productivity or conversion when 20 mole % of N2 is replaced with HCl, i.e., HCl acts as an inert diluent within the reaction system. Also, recycling of methylene chloride (M2) provides no advantageous increase in reactor efficiency, while recycling up to 2 wt % of chloroform (M3) in carbon tetrachloride/perchloroethylene (M4/Perc) feed into the reactor can provide an increase of about 15% increase in reactor productivity.

EXAMPLE 3

Reaction of the Chlorinated and/or Fluorinated Alkanes and Chlorinated and/or Fluorinated Alkenes Methyl Fluoride and Perchloroethylene to Produce the Chlorinated and/or Fluorinated Propene 1,1,2-chloro-3-fluoro-propene An empty Hasteloy tube of 10 inch length and 1 inch diameter is used to run the reaction. Constant methyl fluoride, perchloroethylene and carbon tetrachloride flow is provided to, and maintained in, the reactor whereas flows of the by-products hydrogen chloride, chlorofluoromethane, and chloroform are varied to obtain specific mole percent of flow to the reactor. More specifically, the flow of HCl is varied from 0 mole % to 20 mole % the flow of chlorofluoromethane is varied from 0 mole % to 1.5 mole % and the flow of chloroform is varied from and 0 mole % to 0.8 mole %, in the feed stream to the reactor. In this example, chlorofluoromethane and chloroform are the intermediate boiler by-products.

Reaction temperature is obtained by externally heating the reactor tube. The feed is typically preheated to 325° C. and reactor temperature can be varied between 400° C. to 430° C. The impact of the presence of the by-products hydrogen chloride, chlorofluoromethane and chloroform on perchloroethylene conversion is investigated at a fixed temperature and residence time.

It is expected that HCl will have little or no impact on improving reactor productivity or conversion, i.e., HCl is expected to act as an inert diluent within the reaction system. Also, it is expected that recycling of chlorofluoromethane will provide no advantageous increase in reactor efficiency, while recycling up to 2 wt % of chloroform in carbon tetrachloride/perchloroethylene feed into the reactor can provide an increase of about 15% increase in reactor productivity.

EXAMPLE 4

Reaction of the Chlorinated and/or Fluorinated Alkanes and Chlorinated and/or Fluorinated Alkenes Methylene Chloride and Trichloroethylene to Produce the Chlorinated and/or Fluorinated Propene 1,1,3,3-tetrachloropropene An empty Hasteloy tube of 10 inch length and 1 inch diameter is used to run the reaction. Constant methylene chloride, trichloroethylene and carbon tetrachloride flow is provided to, and maintained in, the reactor whereas flows of the by-products hydrogen chloride, and chloroform are varied to obtain specific mole percent of flow to the reactor. More specifically, the flow of HCl is varied from 0 mole % to 20 mole % the flow of chloroform is varied from and 0 mole % to 0.8 mole %, in the feed stream to the reactor. In this example, only chloroform is the intermediate boiler by-products.

Reaction temperature is obtained by externally heating the reactor tube. The feed is typically preheated to 325° C. and reactor temperature can be varied between 400° C. to 430° C. The impact of the presence of the by-products hydrogen chloride and chloroform on trichloroethylene conversion is investigated at a fixed temperature and residence time.

It is expected that HCl will have little or no impact on improving reactor productivity or conversion, i.e., HCl is expected to act as an inert diluent within the reaction system. Also, it is expected that recycling up to 2 wt % of chloroform (M3) in carbon tetrachloride/trichloroethylene (M4/TCE) feed into the reactor can provide an increase of about 15% increase in reactor productivity.

EXAMPLE 5

Reaction of the Chlorinated and/or Fluorinated Alkanes and Chlorinated and/or Fluorinated Alkenes Methyl Fluoride and Chlorotrifluoroethylene to Produce the Chlorinated and/or Fluorinated Propene 1,1,2,3-tetrafluoropropene An empty Hasteloy tube of 10 inch length and 1 inch diameter is used to run the reaction. Constant methylfluoride, chlorotrifluoroethylene and carbon tetrachloride flow is provided to, and maintained in, the reactor whereas flows of the by-products hydrogen chloride, chlorofluoromethane, and chloroform are varied to obtain specific mole percent of flow to the reactor. More specifically, the flow of HCl is varied from 0 mole % to 20 mole % the flow of chlorofluoromethane is varied from 0 mole % to 1.5 mole % and the flow of chloroform is varied from and 0 mole % to 0.8 mole %, in the feed stream to the reactor. In this example, chlorofluoromethane and chloroform are the intermediate boiler by-products.

Reaction temperature is obtained by externally heating the reactor tube. The feed is typically preheated to 325° C. and reactor temperature can be varied between 400° C. to 430° C. The impact of the presence of the by-products hydrogen chloride, chlorofluoromethane and chloroform on chlorotrifluoroethylene conversion is investigated at a fixed temperature and residence time.

It is expected that HCl will have little or no impact on improving reactor productivity or conversion, i.e., HCl is expected to act as an inert diluent within the reaction system. Also, it is expected that recycling of chlorofluoromethane will provides no advantageous increase in reactor efficiency, while recycling up to 2 wt % of chloroform (M3) in carbon tetrachloride/chlorotrifluoroethylene feed into the reactor can provide an increase of about 15% increase in reactor productivity.

EXAMPLE 6

Hydrofluoroolefins are prepared from the chlorinated and/or fluorinated propenes prepared according to Examples 1-4 by any of several methods known in the art. For example, the conversion of 1,1,2,3-tetrachlororopropene to HFO-1234yf using HF with Chromium/Cobalt base catalyst may be prepared in accordance with the methodology described in WO2008054781A1. WO 2009003084 describes a multi-step process wherein a feedstock of 1,1,2,3 tetrachloropropene is fluorinated in a liquid phase without a catalyst followed by a catalyzed, gas phase reaction to form 2-3,3,3-tetrafluoropropene (HFO1234yf) that is also suitable. US20090030244A1 describes the production of HFO-1234yf using 1,1,2,3-tetrachloropropene using a catalytic process with HF with HCFC-1233xf as intermediate, and this process may also be used. Finally, US20090099396A1 describes a suitable a liquid phase catalytic reaction followed by gas-phase reaction of 1,1,2,3-tetrachloropropene with HV with HFC-245eb as an intermediate. Each of these patent documents is hereby incorporated by reference herein in its entirety for any and all purposes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A continuous, gas phase, free radical process for the production of chlorinated and/or fluorinated propene and higher alkenes from chlorinated and/or fluorinated alkanes and/or chlorinated and/or fluorinated alkenes, wherein at least a portion of any by-products with boiling points in between those of two reactants and generated by the process are removed from the process.

2. The process of claim 1, wherein the chlorinated and/or fluorinated alkanes have the formula $CH_{4-a-b}Cl_aF_b$, wherein a and b are each independently 0-3 and 4-a-b is at least one.

3. The process of claim 2, wherein the chlorinated and/or fluorinated alkanes comprise methyl chloride, methyl fluoride, or methylene chloride.

4. The process of claim 1, wherein the chlorinated and/or fluorinated propene/higher alkene comprises from about three to about six carbon atoms.

5. The process of claim 4, wherein the chlorinated and/or fluorinated propene/higher alkene has the formula $CH_{2-c-g}Cl_cF_g=CH_{1-d-h}Cl_dF_h—CH_{3-e-f}Cl_eF_f$ wherein c is 0-2, d is 0-1, e is 0-3, f is 0-3, and g is 0-2 while c+g≤2, d+h≤1, and e+f≤3.

6. The process of claim 5, wherein the chlorinated and/or fluorinated propene/higher alkene comprises 1,1,2,3-tetrachloropropene, 1,1,3,3-tetrachloropropylene, 1,1,2,3-tetrafluoropropylene, or 1,1,2-chloro-3-fluoro-propene.

7. The process of claim 1, wherein the portion of the by-products are removed from the process via purging a fraction of reactant recycle streams and/or utilization of a conventional distillation, or use of a dividing wall column.

8. The process of claim 1, wherein up to about 5 mole percent in the overall feed stream of at least one by-product is allowed to remain in the process.

9. The process of claim 1, comprising at least one limiting reactant having a desired mass or molar conversion that is less than 40% of exhaustion of a limiting reactant.

10. The process of claim 1, wherein the process comprises at least one thermally sensitive component selected from the group consisting of a reactant, product, byproduct, catalyst, or combinations of these.

11. The process of claim 10, wherein the thermally sensitive component comprises a catalyst comprising chlorine.

12. The process of claim 1, further comprising one or more of i) reducing fouling within the process and/or minimizing the impact of any fouling that may occur, ii) recycling at least a portion of any unreacted reactants, products, by-products and/or diluents, and/or iii) purification of at least one product and/or byproduct of the reaction.

13. The process of claim 12, wherein reducing fouling within the process comprises incorporating a diluent into the process, wherein the diluent is a byproduct of the process.

14. The process of claim 12, wherein the impact of fouling within the process is minimized by operating with at least two reactors, so that if one reactor becomes fouled, the fouled reactor may be shut down and cleaned while the other reactor(s) allow the process to operate substantially continuously.

15. The process of claim 12, wherein reducing fouling within the process comprises removing additional intermediates, contaminants and/or by-products from the process.

16. The process of claim 12, comprising at least two of i) reducing fouling within the process and/or minimizing the impact of any fouling that may occur, ii) recycling at least a portion of any unreacted reactants, products, by-products and/or diluents, and/or iii) purification of at least one product and/or byproduct of the reaction.

17. The process of claim 12, comprising at least three of i) reducing fouling within the process and/or minimizing the impact of any fouling that may occur, ii) recycling at least a portion of any unreacted reactants, products, by-products and/or diluents, and/or iii) purification of at least one product and/or byproduct of the reaction.

* * * * *

UNITED STATES PATENT AND TRADEMARK OFFICE
CERTIFICATE OF CORRECTION

PATENT NO.        : 8,581,012 B2
APPLICATION NO.   : 12/901451
DATED             : November 12, 2013
INVENTOR(S)       : Max M. Tirtowidjojo et al.

It is certified that error appears in the above-identified patent and that said Letters Patent is hereby corrected as shown below:

On the title page, item (73), Assignee, "Dow Global Technologies, LLC" should read "Dow Global Technologies LLC"

Signed and Sealed this
Eleventh Day of November, 2014

Michelle K. Lee
*Deputy Director of the United States Patent and Trademark Office*